(12) United States Patent
Levecq et al.

(10) Patent No.: US 7,862,174 B2
(45) Date of Patent: Jan. 4, 2011

(54) METHOD AND DEVICE FOR MEASURING THE LOCAL SCATTERING OF AN OPTICAL SYSTEM

(75) Inventors: Xavier Jean-Francois Levecq, Gif sur Yvette (FR); Fabrice Harms, Orsay (FR)

(73) Assignee: Imagine Eyes, Orsay (FR)

( * ) Notice: Subject to any disclaimer, the term of this patent is extended or adjusted under 35 U.S.C. 154(b) by 210 days.

(21) Appl. No.: 12/191,808

(22) Filed: Aug. 14, 2008

(65) Prior Publication Data

US 2010/0039619 A1    Feb. 18, 2010

(51) Int. Cl.
*A61B 3/10*    (2006.01)
(52) U.S. Cl. ........................ 351/221; 351/246
(58) Field of Classification Search ............... 351/205, 351/206, 212, 221, 246, 247
See application file for complete search history.

(56) References Cited

U.S. PATENT DOCUMENTS 6,155,684 A    12/2000  Bille et al.
6,382,795 B1    5/2002  Lai
7,255,442 B2    8/2007  Bucourt et al.
2002/0097376 A1    7/2002  Applegate et al.
2004/0189941 A1*    9/2004  Bucourt et al. ............... 351/213
2009/0073384 A1*    3/2009  Warden et al. ............... 351/221

* cited by examiner

*Primary Examiner*—Huy K Mai
(74) *Attorney, Agent, or Firm*—Greer, Burns & Crain, Ltd.

(57) ABSTRACT

A method for measuring, in a given plane, the scattering of an optical system, including:
the illumination of the system by a point source emitting a light flux to be transmitted by the system, and including a direct flux component and a flux component scattered by the system;
the interception of part of the transmitted flux by a sampler positioned in a plane, the intercepted flux including the direct flux component and a narrow angle of the scattered flux component;
the measurement of the intercepted flux by an analyser including an array of microlenses and first image detector, each microlens forming the image of the sampler on the first image detector, the dimensions of the sampler being defined such that the images of the sampler formed by adjacent microlenses present an overlap zone smaller than the projection zone of a microlens on the image detector.

10 Claims, 3 Drawing Sheets

METHOD AND DEVICE FOR MEASURING THE LOCAL SCATTERING OF AN OPTICAL SYSTEM

The present invention relates to the field of optical metrology in general. More specifically, it covers the field of the measurement of local scattering of an optical system and of the optical system of the eye in particular.

STATE OF THE ART

Numerous instruments are used for the objective measurement of the characteristics of the eye. These instruments allow in particular a precise definition of vision-correcting elements, the provision of a support for corrective eye surgery, the detection of ocular pathologies, and more generally, the provision of precise measurements to any device requiring knowledge of the aberrations of the eye.

The device described in the French patent application FR 2 828 396 in the name of the applicant, the content of which is incorporated by way of reference in the present application, describes a device for measuring optical aberrations of the eye. This device, illustrated in FIG. 1, comprises in particular an illumination path VE of the eye EYE with means for emitting an illumination beam FE in order to form a secondary light source by backscattering on the retina RET of the eye, and means MA for analysing the phase of the wave front emitted by said secondary source and emerging from the eye. These analysis means are for example formed by a Shack-Hartmann type analyser, comprising an array of microlenses and detection means (not shown in FIG. 1). In this device in particular, a system of optical filtering elements APT, FLT, allows optimisation of the yield between the light flux incident on the retina and the flux FA received by the analysis means for the determination of the aberrations, by reducing the effect of stray reflections.

Apart from the optical aberrations of the eye, it is important to know the local scattering of the eye, i.e. the scattering measured at any point on a plane of the eye, for example the pupil, the scattering being due to opaque fine particles present in the crystalline lens in particular, or on the cornea.

The American patent application U.S. Pat. No. 6,659,613 describes a principle of measuring the scattering of an optical system and of the eye in particular. The principle rests on the detailed exploitation of the signal originating from the camera of a Shack-Hartmann type wave front analyser and is based on the postulate that each spot of the analyser is the result of the convolution of three phenomena, namely the aberrations of the optical measuring system, the aberrations and the scattering of the optical system that it is desired to characterize. The scattering would then be calculated by deconvolving each spot of the analyser by the theoretical spot calculated by estimation by known methods of the first two phenomena, aberrations of the optical measuring system, and aberrations of the optical system that it is sought to characterize.

However, when it is sought to apply it to the eye, this method suffers from two major drawbacks. Firstly, it is based on the hypothesis that the source which allowed the production of the analysis figure of the Shack-Hartmann analyser is perfectly punctiform (spatially coherent). However, the secondary light source, created on the retina and which serves as "point source" for the Shack-Hartmann measurement, is not a point source. Indeed, the light which is focused on the retina in order to form this secondary source has passed through the optical system of the eye which is not perfect. On the other hand, the retina is a partially transparent and extremely scattering system, like all human tissues and the light which focuses above cannot form a point spot on the surface, but scatters inside, forming a large spot with an apparent diameter several times greater than the diameter of the incident beam focused on its surface. Moreover, the value of this scattering inside the retina is not a constant in the eye and varies from one retina to another and even from one place on the retina to another. It is therefore not possible to use a gauge or a rule which would allow this parameter to be taken into account as part of the deconvolution calculation proposed in the patent.

The other drawback of the proposed method is that it can be applied only within the framework of extremely directional scattering along the axis, the angle of scattering of which would be of the same order of magnitude or smaller than the field of each of the microlenses. The field of a microlens is defined at the detection means as being equal to the projection surface of said microlens on said detection means. Indeed, if the angle of scattering is greater than the field of a microlens, which is the case of the scattering of the optical elements of the eye, the spread of the flux due to the scattering will be greater than the size of a microlens and will also spread to the zone covered by the adjacent spots, making the thus-proposed calculation of the scattering inapplicable.

The present invention allows a local scattering of an optical system, and in particular of the eye, to be measured, by resolving the problems presented above.

SUMMARY OF THE INVENTION

According to a first aspect, the invention relates to a method for measuring, in a given measurement plane, the local scattering of an optical system, comprising:

the illumination of the optical system by means of a point or quasi-point source emitting a light flux intended to be transmitted by the optical system, such that said transmitted flux comprises a component of direct flux and a component of flux scattered by said system;

the interception of a central part of the transmitted flux by means for sampling the flux, of given dimensions, positioned in a plane conjugated with the plane of said source, the intercepted flux comprising the direct flux component and a part called narrow angle of the scattered flux component;

the measurement of the intercepted flux by means of an analyser comprising an array of microlenses positioned in an image plane of the measurement plane and first means for detecting an image, each microlens forming the image of said sampling means on the first image detection means, the dimensions of the sampling means being defined such that the images of the sampling means formed by adjacent microlenses present an overlap zone smaller than the projection zone of a microlens on the image detection means;

the determination of the narrow angle part of the scattered flux component by the measurement of the flux in each overlap zone.

According to a variant, the method also comprises the interception of a peripheral part of the transmitted flux, separate from said central part, on second image detection means positioned in a plane conjugated with the measurement plane, in order to measure a part called wide angle of the scattered flux component.

According to a variant, the method also comprises the measurement of the local transmission of the optical system by means of the measurement, by the first image detection means, of the direct flux component intercepted by each microlens and the normalization of the local scattering component by the local transmission.

According to a variant, the method is applied to the measurement, in a given measurement plane, of the local scattering of the optical system of the eye and also comprises the illumination of the eye in order to form a secondary source on the retina, the transmitted flux being the flux emitted by said secondary source after passing through the optical system of the eye.

According to a second aspect, the invention relates to a device for measuring in a given measurement plane, the local scattering of an optical system, comprising:

a point or quasi-point source emitting a light flux intended to be transmitted by the optical system, such that said transmitted flux comprises a component of direct flux and a component of flux scattered by said system;

a first imaging path comprising means for sampling a central part of the transmitted flux, of given dimensions, positioned in a plane conjugated with the plane of said source, allowing the interception of the direct flux component and of a part called narrow angle of the scattered flux component;

an array of microlenses positioned in an image plane of the measurement plane, first means for detecting an image, each microlens forming the image of said sampling means on the first image detection means, the dimensions of the sampling means being defined such that the images of the sampling means formed by adjacent microlenses present an overlap zone smaller than the projection zone of a microlens on the image detection means, and means for calculating the narrow angle part of the scattered flux component, by measuring the flux in each overlap zone.

According to a variant, the device also comprises a second imaging path, with means for sampling a peripheral part of the transmitted flux, separate from said central part, and second image detection means positioned in a plane conjugated with the measurement plane and receiving said peripheral part of the transmitted flux and means for calculating a part called wide angle of the scattered flux component, from the measurement of the peripheral part of the flux received by the second imaging means.

According to a variant, the sampling means are formed of a reflecting element of predetermined dimensions, allowing the reflection of the central part of the transmitted flux to the first imaging path, and positioned such that that the non-intercepted flux is sent to the second imaging path, thus forming the peripheral part of the flux.

According to a variant, the sampling means are formed of a reflecting element provided with an aperture of predetermined dimensions, allowing the transmission of the central part of the transmitted flux to the first imaging path, and the reflection of the peripheral part of the flux, and positioned such that the reflected flux is sent to the second imaging path.

According to a variant, the device is a device for measuring, in a given measurement plane, the local scattering of the optical system of the eye and also comprises means for illuminating the eye in order to form a secondary source on the retina, the transmitted flux being the flux emitted by said secondary source after passing through the optical system of the eye.

BRIEF DESCRIPTION OF THE FIGURES

Other advantages and features of the invention will appear more clearly on reading the following description, illustrated by the figures which represent.

DESCRIPTION OF EMBODIMENTS

Figure 2:
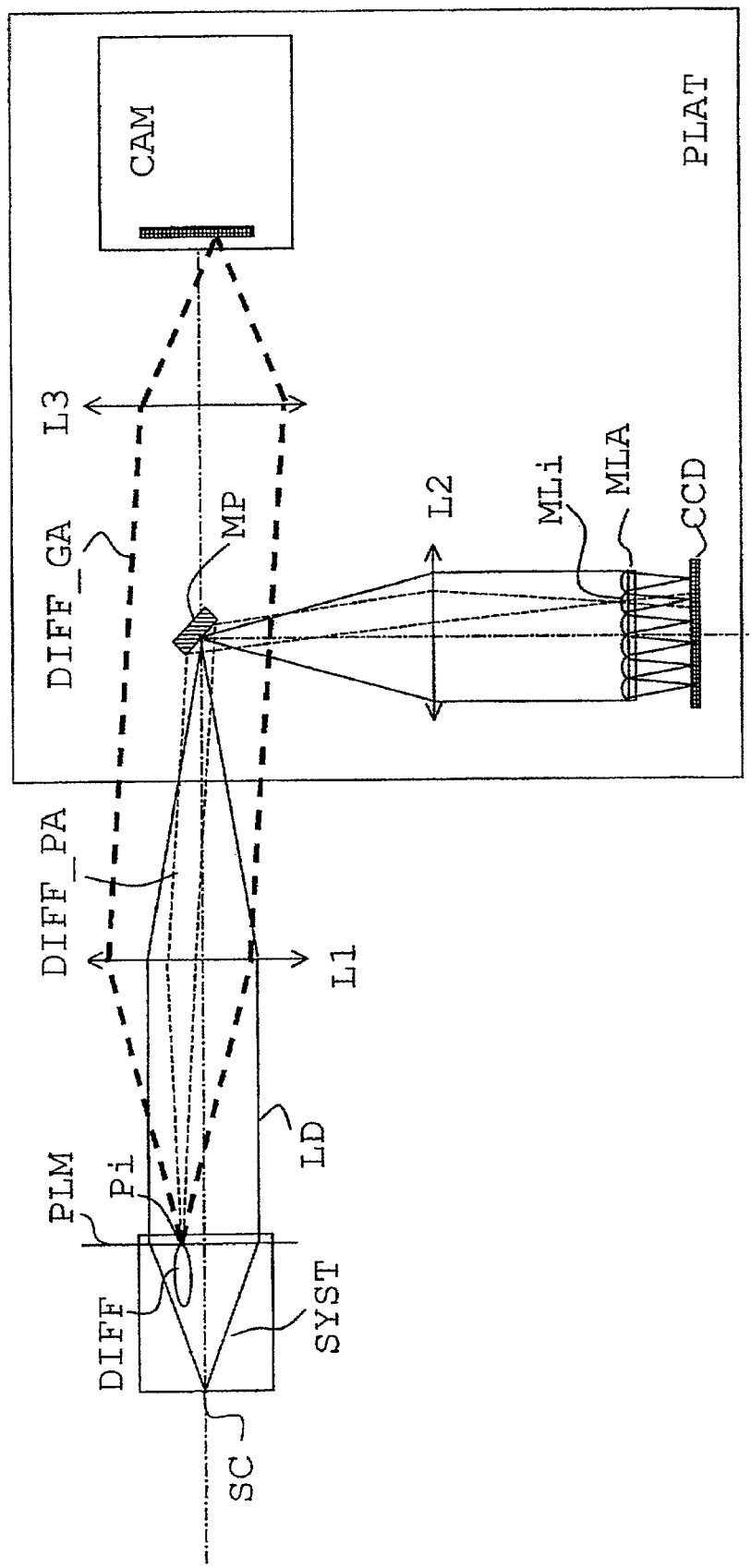
FIG. 2, a diagram of a device for measuring scattering according to the invention.

FIG. 2 represents a diagram of an example of a device for measuring the local scattering of an optical system SYST according to the invention. In this example, the optical system is a system presenting local scattering zones, the establishment of a mapping of which in a measurement plane PLM is sought. The device comprises in particular a point or quasi-point source SC, emitting a light flux intended to be transmitted by the optical system, a first imaging path with means MP for sampling a central part of the transmitted flux, an array of microlenses MLA positioned in a plane optically conjugated with the measurement plane by imaging means L1, and first image detection means CCD. According to this example, the device also comprises a second imaging path with second image detection means CAM and imaging means (L1, L2) allowing the second image detection means to be optically conjugated with the measurement plane PLM.

When the light beam originating from the spatially coherent source SC passes through the optical system SYST, it spreads generally according to the laws of refraction of the optical elements of the system, forming what is hereafter called direct light, or direct light flux, LD. But when the flux passing through the optical system meets a scattering zone DIFF, a part of the direct light LD is dispersed angularly to form a scattered light flux. The scattered light flux can be broken down into several components according to the scattering angle. By "narrow angle" component (DIFF_PA) is meant hereafter the component of the scattered flux which is intercepted with the direct light LD by the sampling means MP. By "wide angle" component (DIFF_GA) is meant hereafter the peripheral component of the scattered flux, not intercepted by the sampling means MP and which reaches as far as the second detection means CAM.

Figure 4:
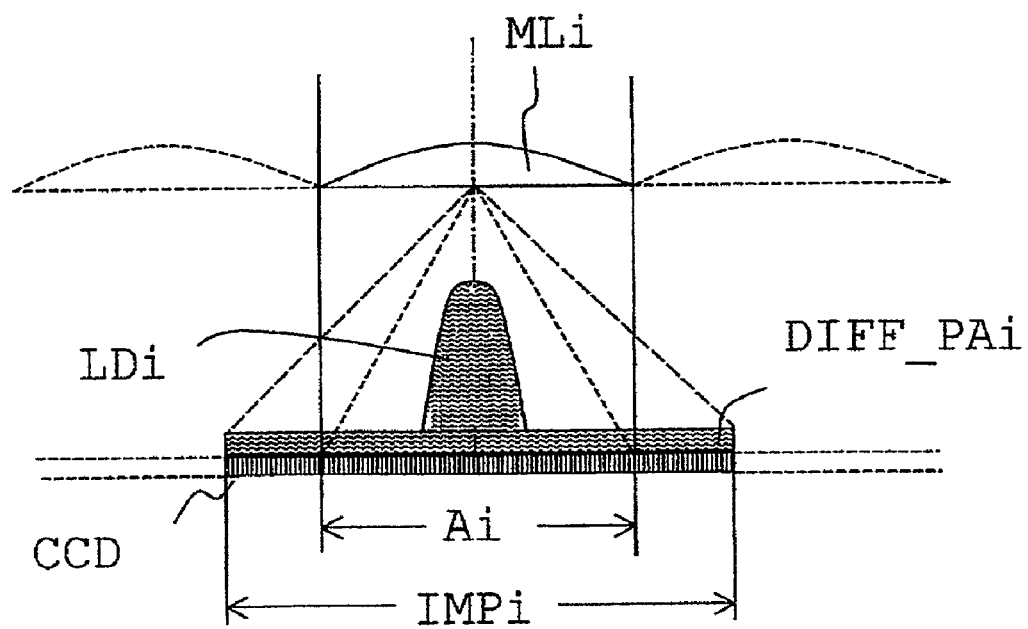
FIG. 4, a diagram showing the distribution of the light flux at the focal point of a microlens.

The light incident on the detector CCD at the focusing plane of each microlens of the array MLA therefore contains part of the direct light LDi and part of the narrow angle scattering component DIFF_PAi, as illustrated in FIG. 4. The direct light part is focussed on a spot LDi of small dimension, whereas the narrow angle scattered light part spreads substantially uniformly over the surface covered by the image IMPi of the sampling means MP formed by each considered microlens MLi.

According to the invention, the dimensions of the sampling means MP are determined so as to control the size of the illuminated zone at the focusing plane of each microlens. This latter must be significantly larger than the zone covered by the focusing spot linked to the direct light and must be small enough for the scattered light part that has passed through each microlens MLi to remain localized in the area around the latter. In fact, within the framework of the determination of the local scattering, it is imperative that the scattered light measured under or in the area immediately around the microlens MLi can be unambiguously allocated to the position of a point Pi on the measurement plane PLM. This measurement point is the optical conjugate of the microlens MLi. The dimensions of the sampling means MP are preferably determined so that its image in the focusing plane of each microlens MLi is comprised between one and two times the projection surface Ai of a microlens on the detection means, hereafter called field of the microlens MLi.

For example, in an optical configuration of the type shown diagrammatically in FIG. 2, a square geometry of the microlenses is chosen, of the order of 100 μm per side, a focal length of the order of 2 mm for each microlens. The light flux incident on the array of microlenses is substantially parallel. A rectangular reflection element is chosen as sampling means, such that the image of this reflection element at the focal point of each microlens covers a square surface, the size of the side of which is equal to approximately 1.5 times the field Ai of a microlens, i.e. approximately 150 μm per side. The dimensions of the reflection element can then be deduced as a function of the focal values of the imaging means L1, L2. In the example chosen, for a focal length of the lens L1 equal to 80 mm and for a focal length of the lens L2 equal to 40 mm for example, the reflection element will be a rectangle measuring approximately 3 mm by 4.24 mm. It would also be possible to choose other embodiments of the sampling means MP. For example, it could be a reflection element pierced in its centre by an aperture of predetermined dimensions, the direct flux and the narrow angle scattered flux being transmitted through the aperture to the first imaging path. Such a configuration is close to that represented in FIG. 1.

Figure 3:
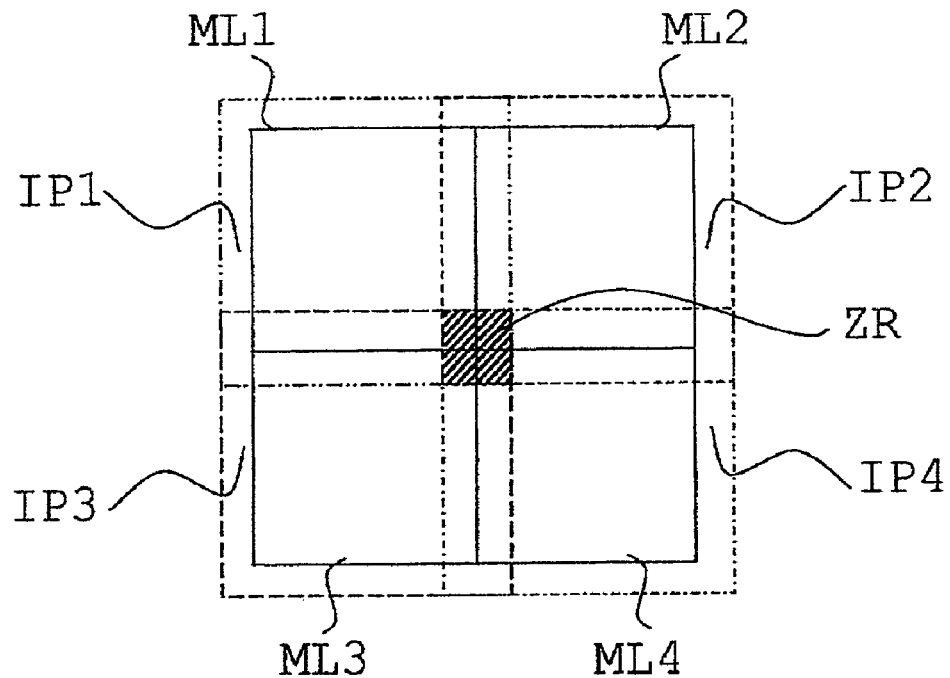
FIG. 3, a diagram explaining the determination of the part called narrow angle of the scattered flux.

FIG. 3 shows the covering of the images IP1, IP2, IP3, IP4 of the sampling means MP at the focusing plane of 4 adjacent microlenses ML1, ML2, ML3, ML4. As illustrated in FIG. 3, it is advantageous to have the image of the sampling means at the focusing plane of each microlens larger than the field of a microlens. In this case in fact, an overlap zone ZR of the 4 narrow angle scattering zones (IP1 to IP4) and a significant increase in the signal-to-noise ratio of the measurement are obtained, due to the summation of the signals DIFF_PAi intercepted by the 4 adjacent microlenses.

The measurement of the narrow angle scattering, at a point Pi of the measurement plane, is obtained as follows. An overlap zone is attributed to a microlens. For example, as in FIG. 3, the overlap zone is constituted by the intersection of the narrow angle scattering parts of the fluxes intercepted by the microlenses ML1, ML2, ML3, ML4. According to a first variant, the measurement of the flux over the overlap zone gives a value of the local scattering (narrow angle) at the measuring point corresponding to the microlens to which the overlap zone is attributed. In this case there is a mapping of the narrow angle local scattering, with for each point, a value summed over 4 adjacent points. Optionally, to increase spatial resolution, means for processing the signal allow calculating the narrow field local scattering of each point, without the contribution of the adjacent points.

This measurement assumes that the direct flux on the overlap zone is negligible. In the case of very aberrant optical systems, such as for example the optical system of the eye, in particular when it is blemished by a strong astigmatism, the light spot LDi corresponding to the direct flux intercepted by part of the microlenses can shift in the field of the microlens and superimpose itself on the overlap zone. According to the invention, it is possible to eliminate this fault by carrying out several measurements of the narrow angle local scattering, for each of these measurements, the imaging path comprising the sampling and analysis means being moved transitionally, for example thanks to the translational movement of the platform PLAT, represented in FIG. 2. In fact, any shift of the platform involves a shift of the direct flux spots in the focusing plane of each of the microlenses. For each measurement, the narrow angle local scattering value is recorded, then only the smallest of the values is kept, which will necessarily correspond to the value least blemished by a contribution of the aberrant direct flux. The positions of the platform are chosen so as to obtain an adequate shift of the direct flux spots.

According to a variant, the narrow angle local scattering measurement is normalized by the local value of the transmission of the optical system. This can be obtained by the measurement, using the first image detection means (CCD), of the direct flux component intercepted by each microlens.

Advantageously, the narrow angle scattering measurement is supplemented by what is called a wide angle scattering measurement, carried out using the second imaging path. This imaging path allows the measurement of the peripheral part of the scattered flux, called wide angle part, separate from said central part of the scattered flux, and corresponding in the example of FIG. 2 to the part of the flux not intercepted by the sampling means MP. The wide angle part of the scattered flux (DIFF_GA) is focussed by means of an objective L3 on the second image detection means CAM, for example a CCD- or CMOS-type detector, optically conjugated with the measurement plane PLM. In this way a mapping of the wide angle local scattering is obtained directly at the measurement plane. As previously, the wide angle scattering value can be normalized by the local value of the transmission of the optical system.

Two mappings in the measurement plane PLM, corresponding respectively to the narrow angle and wide angle local scattering, are thus obtained. These two mappings can be added together in order to obtain a mapping of the overall component of the scattered flux.

For example, these mappings can be used to supplement measurements of the aberrations of the optical system, in order to calculate the percussional response and the modulation transfer function of the optical system, taking account of the scattering.

Figure 1:
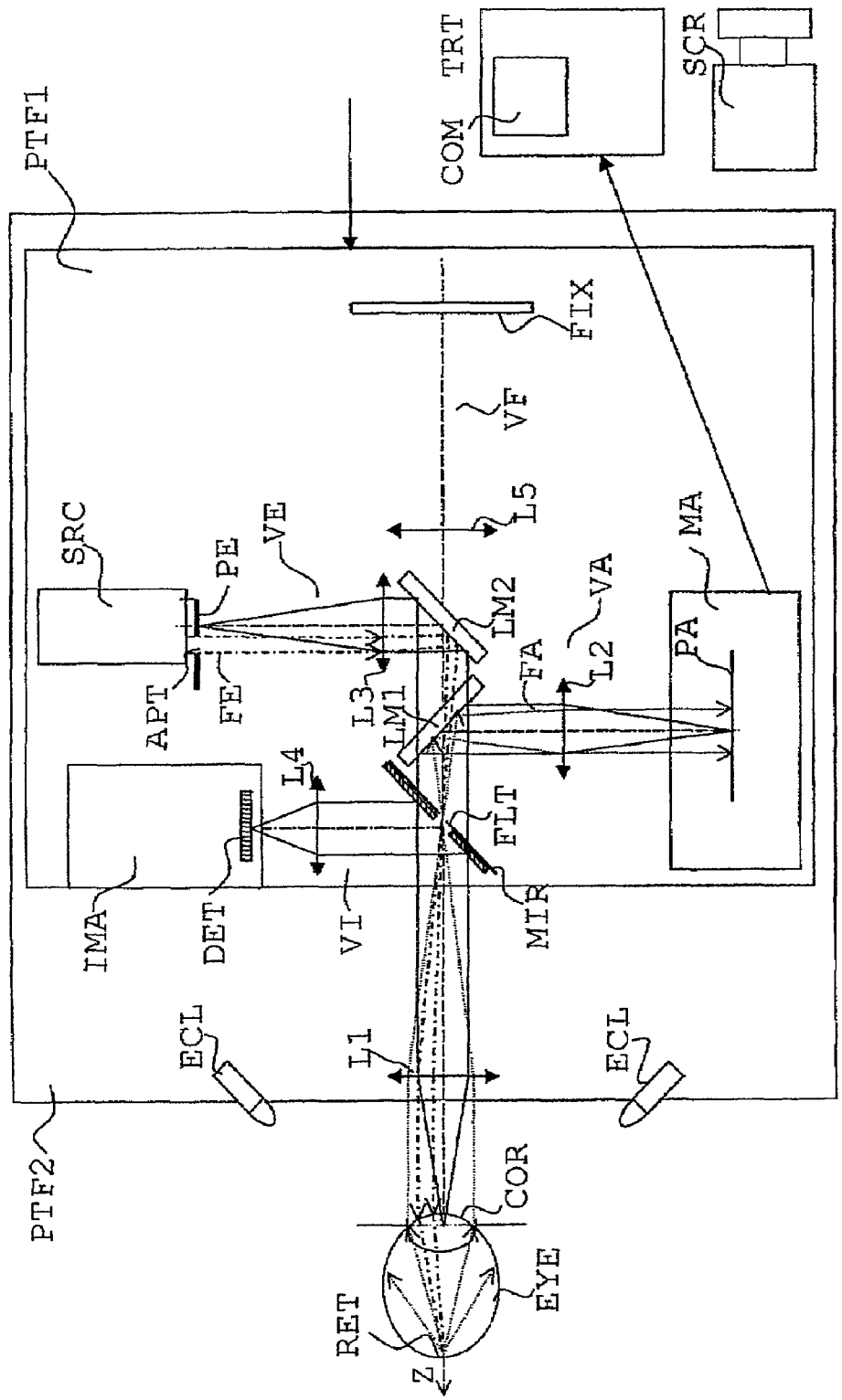
FIG. 1, a device for measuring the aberrations of the eye according to the prior art (already described)

Although the example of FIG. 2 is described for the measurement of the scattering of an optical system in general, it applies fully to the measurement of the optical system of the eye EYE, as illustrated diagrammatically in FIG. 1. The eye comprises the retina, the crystalline lens, the cornea and the aqueous or vitreous humour. In the case of the optical system of the eye, the scattering zones are in general situated in the crystalline lens and the pupil of the eye. The measurement plane is for example that of the pupil. In the case of the analysis of the eye, it is necessary to form a secondary source at the retina. Illumination means such as described for example in FIG. 1 can be used.

The invention has been described by means of particular non-limitative embodiments and is open to variants and modifications which will be apparent to a person skilled in the art.

In particular, the sampling means have been described with a rectangular shape, but they can present different shapes, square, circular, elliptical, etc. provided that the constraint in respect of dimensions is observed in order that each overlap zone remains smaller than the field of a microlens.

The shape of the microlenses can also vary. Advantageously, a similar shape will be chosen for the images of the sampling means and for the microlenses in order to simplify the processing of the signals, but different shapes can also be chosen.

The invention claimed is:

1. A method for measuring, in a predetermined measurement plane, the local scattering of an optical system, comprising:
   the illumination of the optical system by means of a point or quasi-point source emitting a light flux intended to be transmitted by the optical system, such that said transmitted flux comprises a component of direct flux and a component of flux scattered by said optical system;
   the interception of a central part of the transmitted flux by means for sampling the flux, of predetermined dimensions, positioned in a plane conjugated with the plane of said source, the intercepted flux comprising the direct flux component and a part called narrow angle of the scattered flux component;
   the measurement of the intercepted flux by means of an analyser comprising an array of microlenses positioned in an image plane of the measurement plane and first detection means, each microlens forming an image of said sampling means on the first detection means, the dimensions of the sampling means being defined such that the images of the sampling means formed by adjacent microlenses on the first detection means present an overlap zone smaller than the projection zone of a microlens on the first detection means; and
   the determination of the narrow angle part of the scattered flux component by the measurement of the flux in each overlap zone.

2. The method according to claim 1, also comprising:
   the interception of a peripheral part of the transmitted flux, separate from said central part, on second detection means positioned in a plane conjugated with the measurement plane, in order to measure a part called wide angle of the scattered flux component.

3. The method according to claim 1, also comprising:
   the measurement of the local transmission of the optical system by means of the measurement, by the first detection means, of the direct flux component intercepted by each microlens; and
   the normalization of the local scattering component by the local transmission.

4. The method according to claim 1, applied to the measurement, in a predetermined measurement plane, of the local scattering of the optical system of the eye, also comprising:
   the illumination of the eye in order to form a secondary source on the retina, the transmitted flux being the flux emitted by said secondary source after passing through the optical system of the eye.

5. A method according to claim 4, according to which said measurement plane is the plane of the pupil of the eye.

6. A device for measuring, in a determined measurement plane, the local scattering of an optical system, comprising:
   a point or quasi-point source emitting a light flux intended to be transmitted by the optical system, such that said transmitted flux comprises a component of direct flux and a component of flux scattered by said optical system;
   a first imaging part comprising:
      means for sampling a central part of the transmitted flux, of predetermined dimensions, positioned in a plane conjugated with the plane of said source, allowing the interception of the direct flux component and of a part called narrow angle of the scattered flux component;
      an array of microlenses positioned in an image plane of the measurement plane;
      first detection means, each microlens forming the image of said sampling means on the first detection means, the dimensions of the sampling means being defined such that the images of the sampling means formed by adjacent microlenses on the first detection means present an overlap zone smaller than the projection zone of a microlens on the first detection means; and
   means for calculating the narrow angle part of the scattered flux component, by measuring the flux in each overlap zone.

7. A device according to claim 6, also comprising:
   a second imaging part, with means for sampling a peripheral part of the transmitted flux, separate from said central part, and second detection means positioned in a plane conjugated with the measurement plane and receiving said peripheral part of the transmitted flux; and
   means for calculating a part called wide angle of the scattered flux component, from the measurement of the peripheral part of the flux received by the second imaging means.

8. The device according to claim 6, in which the sampling means are formed by a reflecting element of predetermined dimensions, allowing the reflection of the central part of the transmitted flux to the first imaging part, and positioned such that the non-intercepted flux is sent to the second imaging part, thus forming the peripheral part of the flux.

9. The device according to claim 6, in which the sampling means are formed by a reflecting element provided with an aperture of predetermined dimensions, allowing the transmission of the central part of the transmitted flux to the first imaging part, and the reflection of the peripheral part of the flux, and positioned such that the reflected flux is sent to the second imaging part.

10. The device for measuring, in a predetermined measurement plane, the local scattering of the optical system of the eye according to claim 6, also comprising means for illuminating the eye in order to form a secondary source on the retina, the transmitted flux being the flux emitted by said secondary source after passing through the optical system of the eye.

* * * * *